US00PP30155P3

(12) United States Plant Patent
Schoone

(10) Patent No.: US PP30,155 P3
(45) Date of Patent: Jan. 29, 2019

(54) ***PHALAENOPSIS* ORCHID PLANT NAMED 'GOLDEN STORY'**

(50) Latin Name: *Phalaenopsis hybrida*
Varietal Denomination: Golden Story

(71) Applicant: Floricultura, Heemskerk (NL)

(72) Inventor: René Schoone, Assendelft (NL)

(73) Assignee: FLORICULTURA, Heemskerk (NL)

( * ) Notice: Subject to any disclaimer, the term of this patent is extended or adjusted under 35 U.S.C. 154(b) by 0 days.

(21) Appl. No.: 15/731,129

(22) Filed: Apr. 25, 2017

(65) Prior Publication Data

US 2017/0311517 P1 Oct. 26, 2017

Related U.S. Application Data

(60) Provisional application No. 62/327,814, filed on Apr. 26, 2016.

(30) Foreign Application Priority Data

Apr. 29, 2016 (NL) ..... PBR OPS1327

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
CPC ... A01H 5/02; A01H 5/00; A01H 5/08; A01H 6/62
See application file for complete search history.

(56) References Cited

U.S. PATENT DOCUMENTS

PP26,724 P3 * 5/2016 Schoone ..... A01H 5/02 Plt./311

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Golden Story' particularly characterized by flowers which are yellow/green; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Golden Story'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Golden Story'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Golden Story' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Golden Story' originated from a cross made by the inventor in 2003 in Strengweg, Heemskerk, The Netherlands. The female or seed parent is an unknown *Phalaenopsis*. The male or pollen parent is an unknown *Phalaenopsis*. The new *Phalaenopsis* 'Golden Story' was discovered and selected by the inventor as a single flowering plant within the progeny of the stated cross in a controlled environment in 2011 in Strengweg, Heemskerk, The Netherlands.

Asexual reproduction of the new *Phalaenopsis* cultivar by tissue culture (mericloning) was first performed in November, 2011 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Golden Story', which in combination distinguish this *Phalaenopsis* as a new and distinct cultivar:

1. flowers which are yellow/green;
2. plant produces more than one inflorescence;
3. plants may be propagated economically and uniformly using tissue culture;
4. inflorescences are long and sturdy; and
5. relatively short, dark-green foliage.

'Golden Story' cannot be compared with its parental cultivars, because they are unknown.

Presently, the commercial cultivar to which 'Golden Story' can be meaningfully compared is 'Suri', U.S. Plant Pat. No. 26,724 (Schoone). 'Golden Story' has more yellow in the flower. The lateral petals of 'Suri' are more whitish yellow compared to the yellow green of 'Golden Story'. The midlobe of 'Suri' is white, while the upper midlobe of 'Golden Story' is yellow and the lower midlobe is white. The flower of 'Suri' U.S. Plant Pat. No. 26,724 (Schoone) is a little larger in size.

BRIEF DESCRIPTION OF THE PHOTOGRAPHS

The accompanying photographs illustrate the overall appearance of the new *Phalaenopsis* 'Golden Story' showing the colors as true as is reasonably possible with colored reproductions of this type. Colors in the photographs may differ slightly from the color values cited in the detailed botanical description, which accurately describe the color of 'Golden Story'.

DETAILED BOTANICAL DESCRIPTION

Figure 1:
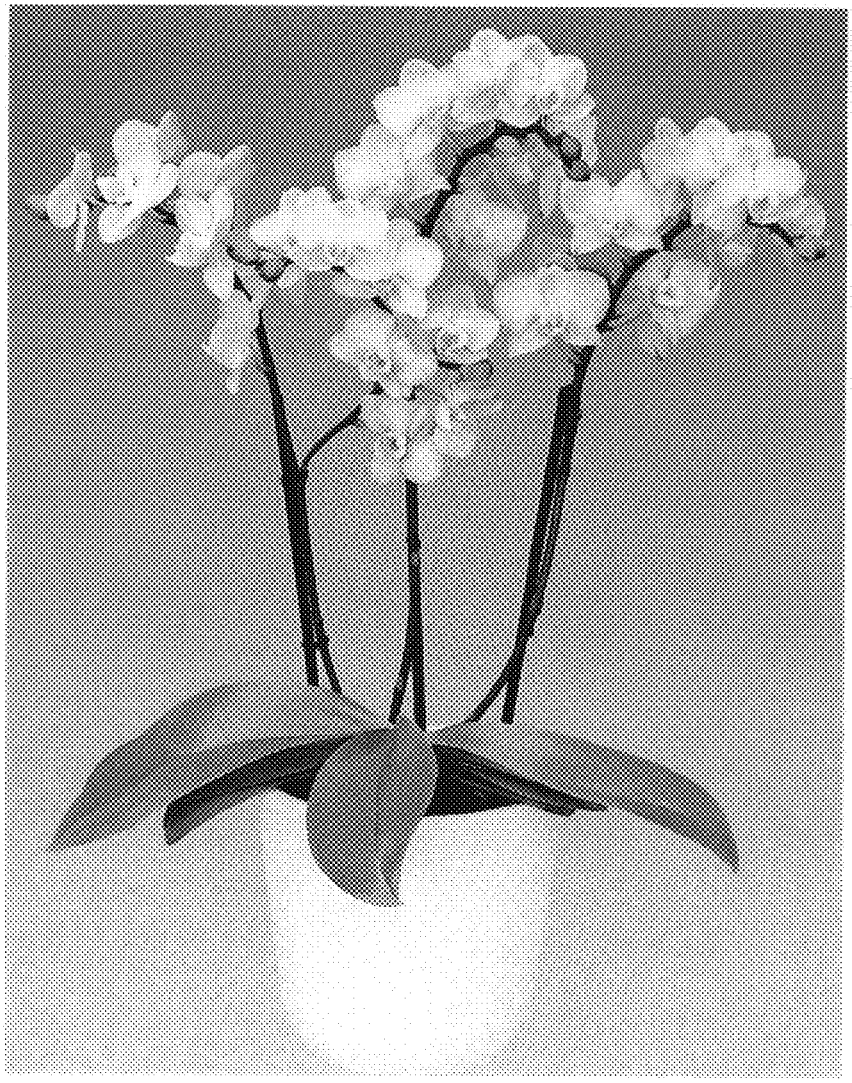
FIG. 1 shows a side view perspective of a typical flowering plant of 'Golden Story' in a 12 cm pot, at 16 months of age.

The new *Phalaenopsis* cultivar 'Golden Story' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Golden Story' as grown in a greenhouse in Strengweg, Heemskerk, The Netherlands, under conditions which closely approximate those generally used in commercial practice. Initially, the ideal temperature to grow plants of 'Golden Story' is 27° C. during the day and at night. Then, during the flowering phase of 'Golden Story', the ideal growing temperature is 20-22° C. during the day and 18° C. at night. Light levels for growing 'Golden Story' are a minimum of 5,000 lux and a maximum of 10,000 lux. A balanced fertilizer with level of 200 ppm N, 87 ppm P, 168 ppm K is applied. Duration of growth of 'Golden Story' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Golden Story' plants described is 12 months after potting.

Classification:

*Botanical.—Phalaenopsis hybrida.*

Parentage:

*Female or seed parent.—Phalaenopsis* 'unknown', unpatented.

*Male or pollen parent.—Phalaenopsis* 'unknown', unpatented.

Propagation:

*Type.*—Tissue culture.

*Rooting habit and description.*—Fleshy; approximately 4 mm-7 mm wide and greyed/green in color (RHS 190A); freely branching. It takes 12 weeks for plants growing in tissue culture to initiate roots.

Plant:

*Size at maturity.*—Height (from bottom of pot to highest flower): about 40 cm. Spread: about 35 cm.

*Growth habit.*—Small; green leaves (RHS 137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6-8 leaves are produced before flowering.

*Arrangement and attachment.*—Alternate, clasping.

*Overall shape of leaf.*—Oval; the tip is blunt and asymmetric.

*Texture (upper & underside).*—Smooth and leathery.

*Pubescence.*—None.

*Mature leaf length.*—About 15 cm.

*Mature leaf width.*—About 7 cm.

*Mature leaf thickness.*—About 2 mm.

*Mature leaf color.*—Upper side: green (RHS 137A). Under side: green (RHS 137B) with at some leaves some greyed/purple (RHS 187B).

*Leaf base.*—Acute.

*Margin.*—Entire.

*Venation.*—Pattern: parallel. Color of midvein: upper side: green (RHS 137A). Under side: green (RHS N137A and RHS N137B) and a few have some greyed/purple at the midvein (RHS 187B).

Inflorescence description:

Appearance: Upright to slightly pendant, racemose inflorescence with bilaterally symmetrical flowers that open in succession beginning with the lowermost flower.

Raceme:

*Quantity per plant.*—About 1 to 3.

*Number of flowers per raceme.*—About 10-17.

*Length.*—About 20 cm.

*Diameter.*—About 30 cm.

Peduncle:

*Length.*—About 8-18 cm.

*Diameter.*—About 4 mm.

*Strength*.—Strong.

*Aspect*.—Upright.

*Texture*.—Glabrous and smooth.

*Color*.—Yellow/green (RHS 144B) with some greyed/purple (RHS N186C).

Buds:

*Height* (*from base to tip*).—About 18 mm.

*Diameter* (*at midpoint*).—About 15 mm.

*Shape*.—Asymmetric oval.

*Color*.—Yellow/green (RHS 144C) with red/purple haze (RHS 59A).

*Orientation*.—Same as flowers (forward facing).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening*.—Flowers fully opened about 2 to 3 days after petal and sepal separation.

*Orientation at opening*.—Slanted upward and outward.

Figure 2:
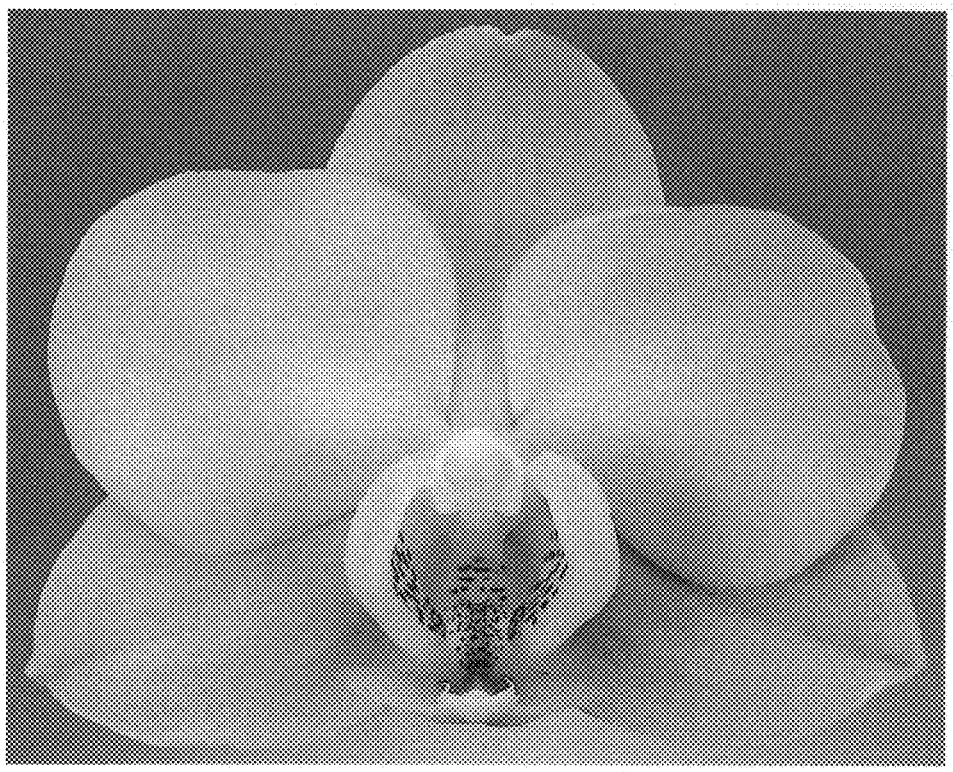
FIG. 2 shows a close-up view of the typical flower of 'Golden Story'.
Figure 3:
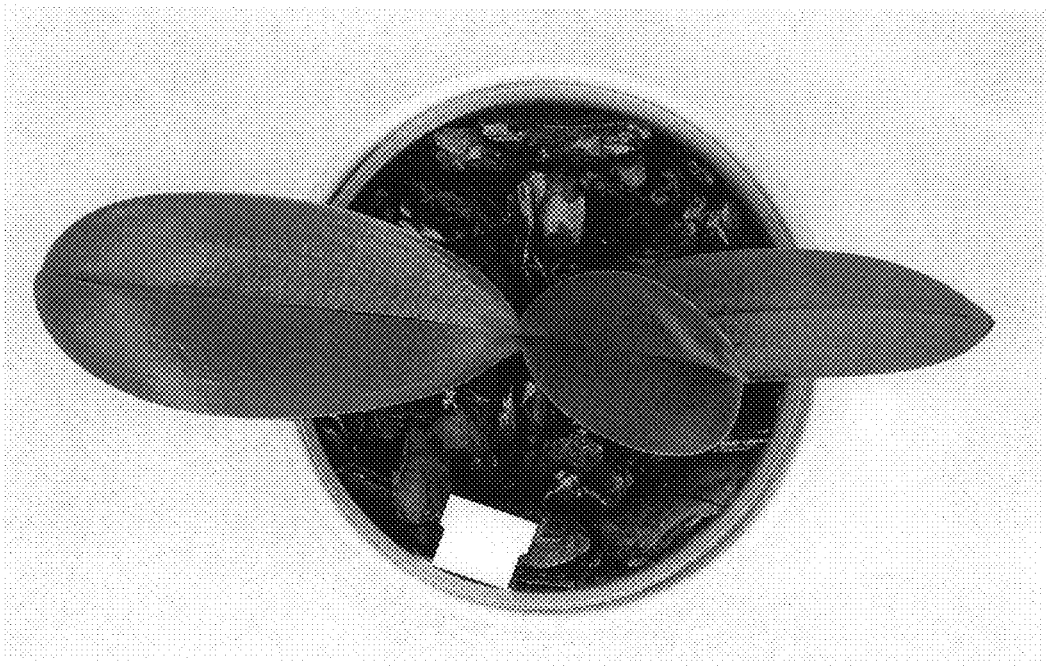
FIG. 3 shows a close-up view of the typical leaves of 'Golden Story'.

*Shape*.—Typical shape of *Phalaenopsis*; see FIG. 2.

*Size* (*of single bloom*).—Height: about 45 mm. Diameter: about 50 mm.

*Quantity and arrangement*.—Three petals and three sepals. Arrangement of petals are free, not touching. Petals are more pronounced than sepals.

Petals:

*Arrangement*.—Inner whorl comprises 3 petals: 2 lateral petals and a labellum.

2 *lateral petals*.—Overall shape: broadly ovate and weakly cupped. Apex: rounded. Margin: entire and weakly undulate. Base: broadly ovate. Length: about 25 mm. Width: about 25 mm. Texture: Upper surface: smooth and satiny. Under surface: smooth and satiny. Color (when fully opened): upper side: yellow/green (RHS 145D and RHS 145C) and closer to base a white haze (RHS NN155C). Under side: yellow/green (RHS 145D and RHS 145C) and closer to base a white haze (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 stub appendages at the apex. Lateral lobes of the labellum are ovate in shape while the midlobe is triangular with a bump and a rib on it. Margin of midlobe and lateral lobes: entire and weakly undulate. Apex of the midlobe and lateral lobes: rounded. Length midlobe: about 18 mm. Width midlobe (not flattened): about 16 mm. Length lateral lobe: about 8 mm. Width lateral lobe (not flattened): about 17 mm. Depth of tube created by lateral lobes of labellum: about 17 mm. Texture of midlobe and lateral lobes: Upper & under surface: smooth and satiny. Color (when fully opened): Mid lobe, upper side: Upper part of the midlobe is yellow (RHS 7A). Lower part of the midlobe is white (RHS NN155C). There are no spots and stripes. Under side: at the base and corners some yellow/green (RHS 145B) and yellow (RHS 7A) which runs into white (RHS NN155C). Lateral lobes, upper side: Main color is white (RHS NN155D). At the base yellow (RHS 7A) and a moderate amount of red/purple stripes and spots (RHS 59A). At the lower edge yellow (RHS 7A). Under side: Main color is white (RHS NN155D). At the base some vague red/purple spots (RHS 59A) and the bottom edge is yellow (RHS 7A). Cirrhi: about 2 mm. Color: white (RHS NN155D). Pestle (Callosities): Length: about 4 mm. Width (not flattened): about 3 mm. Color: Sides are yellow (RHS 13C) and top and edges are yellow (RHS 13A) with red/purple spots (RHS 59A).

Sepals:

*Arrangement*.—Outer whorl comprises 3 sepals, one dorsal and two lateral sepals.

*Overall shape*.—Elliptical and weakly cupped.

*Margin*.—Entire and weakly undulate.

*Length*.—About 25 mm.

*Width*.—About 20 mm.

*Apex*.—Rounded.

*Texture*.—Upper and under surface: smooth and satiny. Color (when fully opened): Upper side, dorsal and lateral: yellow/green (RHS 145C and RHS 145B). Under side, dorsal: yellow/green (RHS 145B) with closer to the edges a lighter yellow/green (RHS 145C). The tip has some red/purple (RHS 59A). Lateral: yellow/green (RHS 145B and RHS 145A) with at the edges yellow/green (RHS 145C). At the tip some red/purple (RHS 59A).

Pedicel:

*Length*.—About 25 mm.

*Diameter*.—About 3 mm.

*Texture*.—Glabrous and smooth.

*Color*.—Yellow/green (RHS 145D and RHS 145D) which runs into yellow/green (RHS 145B and RHS 145A).

Reproductive organs:

Arrangement: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

Column:

*Length*.—About 8 mm.

*Diameter*.—About 3 mm.

*Color*.—White (RHS NN155D).

Pollinia:

*Quantity*.—Two.

*Diameter*.—About 2 mm.

*Color*.—Yellow/orange (RHS 23A).

Ovary:

*Length*.—About 3 mm.

*Diameter*.—About 4 mm.

*Color*.—White (RHS NN155D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Golden Story', as illustrated and described herein.

* * * * *